US009902950B2

(12) United States Patent
Church et al.

(10) Patent No.: US 9,902,950 B2
(45) Date of Patent: Feb. 27, 2018

(54) HIGH-THROUGHPUT SINGLE CELL BARCODING

(75) Inventors: George M. Church, Brookline, MA (US); Francois Vigneault, Medford, MA (US)

(73) Assignee: President and Fellows of Harvard College, Cambridge, MA (US)

(*) Notice: Subject to any disclaimer, the term of this patent is extended or adjusted under 35 U.S.C. 154(b) by 514 days.

(21) Appl. No.: 13/878,406

(22) PCT Filed: Oct. 11, 2011

(86) PCT No.: PCT/US2011/055803
§ 371 (c)(1),
(2), (4) Date: May 21, 2013

(87) PCT Pub. No.: WO2012/048341
PCT Pub. Date: Apr. 12, 2012

(65) Prior Publication Data
US 2013/0274117 A1 Oct. 17, 2013

Related U.S. Application Data

(60) Provisional application No. 61/391,364, filed on Oct. 8, 2010.

(51) Int. Cl.
C12N 15/10 (2006.01)
C12Q 1/68 (2018.01)
C40B 50/16 (2006.01)

(52) U.S. Cl.
CPC ....... *C12N 15/1065* (2013.01); *C12Q 1/6806* (2013.01); *C12Q 1/6869* (2013.01); *C40B 50/16* (2013.01); *B01J 2219/00547* (2013.01); *B01J 2219/00576* (2013.01); *B01J 2219/00722* (2013.01); *C12Q 2600/172* (2013.01)

(58) Field of Classification Search
None
See application file for complete search history.

(56) References Cited

U.S. PATENT DOCUMENTS

| 9,701,998 | B2* | 7/2017 | Hindson | C12Q 1/6806 |
| 2002/0192687 | A1 | 12/2002 | Mirkin et al. | |
| 2004/0185484 | A1 | 9/2004 | Costa et al. | |
| 2006/0008824 | A1 | 1/2006 | Ronaghi et al. | |
| 2008/0090239 | A1* | 4/2008 | Shoemaker | G01N 33/5091 435/6.12 |
| 2008/0241820 | A1 | 10/2008 | Krutzik et al. | |
| 2008/0269068 | A1 | 10/2008 | Church et al. | |
| 2009/0098555 | A1* | 4/2009 | Roth | C12Q 1/6816 435/6.12 |
| 2009/0163366 | A1* | 6/2009 | Nickerson et al. | 506/4 |
| 2010/0035763 | A1* | 2/2010 | Chen | C07K 16/2896 506/9 |
| 2010/0062494 | A1 | 3/2010 | Church et al. | |

FOREIGN PATENT DOCUMENTS

| AU | 2008200151 A1 | 2/2008 | |
| WO | 1998/044151 A1 | 10/1998 | |
| WO | 2000/075374 A1 | 12/2000 | |
| WO | 2001/062982 A2 | 8/2001 | |
| WO | 2007/107710 A1 | 9/2007 | |
| WO | 2008/076842 A2 | 6/2008 | |
| WO | 2010/003132 A1 | 1/2010 | |
| WO | WO 2010117620 A2 * | 10/2010 | ......... C12N 15/1065 |

OTHER PUBLICATIONS

Zeng et al., High-performance single cell genetic analysis using microfluidic emulsion generator arrays, Anal Chem. Apr. 15, 2010;82(8):3183-90.*
Kumaresan et al., High-throughput single copy DNA amplification and cell analysis in engineered nanoliter droplets, Anal Chem. May 15, 2008;80(10):3522-9, Epub Apr. 15, 2008.*
Hug et al., Measurement of the number of molecules of a single mRNA species in a complex mRNA preparation, J Theor Biol. Apr. 21, 2003;221(4):615-24.*
UKIPO Search Report issued from corresponding GB 1308241.7, dated Oct. 15, 2013.
Brenner, Charles, "A cultivated taste for yeast," Genome Biology, Apr. 27, 2000, pp. 103.1-103.4, vol. 1, No. 1.
Brenner,Charles,"Chemical genomics in yeast," Genome Biology, Aug. 27, 2004, pp. 240.1-240.4, vol. 5, issue 9.
Brenner,Sydney, et al.,"In vitro cloning of complex mixtures of DNA on microbeads: Physical separation of differentially expressed cDNAs," PNAS, Feb. 15, 2000, pp. 1665-1670, vol. 97, No. 4.
Chapal, N., et al.,"In-Cell Assembly of scFv from Human Thyroid-Infiltrating B Cells," BioTechniques, Sep. 1997, pp. 518-524, vol. 23, No. 3.
Eason, Robert G., et al.,"Characterization of synthetic DNA bar codes in *Saccharomyces cerevisiae* gene-deletion strains," PNAS, Jul. 27, 2004, pp. 11046-11051, vol. 101, No. 30.
Embleton, M. J., et al.,"In-cell PCR from mRNA: amplifying and linking the rearranged immunoglobulin heavy and light chain V-genes within single cells," Nucleic Acids Research, Jul. 9, 1992, pp. 3831-3837, vol. 20, No. 15, Oxford University Press.
Giaever, Guri, et al.,"Chemogenomic profiling: Identifying the functional interactions of small molecules in yeast," PNAS, Jan. 20, 2004, pp. 793-798, vol. 101, No. 3, The National Academy of Sciences.
Kim, Jae Bum, et al.,"Polony Multiplex Analysis of Gene Expression (PMAGE) in Mouse Hypertrophic Cardiomyopathy," Science, Jun. 8, 2007, pp. 1481-1484, vol. 316, No. 5830, American Association for the Advancement of Science.
Kumar, Anuj, et al.,"Emerging Technologies in Yeast Genomics," Nature Reviews: Genetics, Apr. 2001, pp. 302-312, vol. 2, Macmillan Magazines Ltd.
Porreca, Gregory J., et al.,"Polony DNA Sequencing," Current Protocols in Molecular Biology, 2006, pp. 7.8.1-7.8.22, supplement 76, John Wiley & Sons, Inc.
Winzeler, Elizabeth A., et al.,"Functional Characterization of the *S. cerevisiae* Genome by Gene Deletion and Parallel Analysis," Science, Aug. 6, 1999, pp. 901-906, vol. 285.

(Continued)

*Primary Examiner* — Aaron A Priest
(74) *Attorney, Agent, or Firm* — Banner & Witcoff, Ltd.

(57) ABSTRACT

Methods and compositions for high-throughput, single cell analyzes are provided. The methods and compositions can be used for analysis of genomes and transcriptomes, as well as antibody discovery, HLA typing, haplotyping and drug discovery.

40 Claims, 17 Drawing Sheets

(56) References Cited

OTHER PUBLICATIONS

Zhang, Kun, et al.,"Long-range polony haplotyping of individual human chromosome molecules," Nature Genetics, Mar. 2006, pp. 382-387, vol. 38, No. 3, Nature Publishing Group.
Office Action issued for corresponding United Kingdom Patent Application No. GB1405780.6 dated Jul. 18, 2014.
Extended European Search Report issued from corresponding EP Patent Application No. 11831761.9, dated Mar. 3, 2014.
Alon, Shahar, et al: "Barcoding bias in 1-15 high-throughput multiplex sequencing of mi RNA.". Genome Research Sep. 2011. vol. 21. No. 9. Sep. 2011 (Sep. 2011). pp. 1506-1511. XP002720457. ISSN: 1549-5469 "the whole document ".
Seda,Eminaga, et al: "Quantification of microRNA expression with next-generation sequencing.". Current Protocols in Molecular Biology / Edited by Frederick M. Ausubel . . . [et al.] Jul. 2013. vol. Chapter 4. Jul. 2013 (Jul. 2013). XP002720456. ISSN: 1934-3647 * the whole document * .
Vigneault, Francois et al: "Efficient microRNA capture and barcoding via enzymatic oligonucleotide adenylation". Nature Methods. Nature Publishing Group.GB. vo 1 • 5. No. 9. Sep. 1, 2008 (Sep. 1, 2008). pages 777-779. XP002652586. ISSN: 1548-7091. DOI: 10.1038/NMETH.1244 [retrieved on Aug. 17, 2008].
Office Action issued from corresponding GB Patent Application No. GB1308241.7, dated Jan. 31, 2014.
Office Action issued for corresponding Canadian Patent Application No. 2,814,049, dated Jan. 23, 2015.
Islam, Saiful et al., "Characterization of the single-cell transcriptional landscape by highly multiplex RNA-seq", Genome Research, Cold Spring Harbor Laboratory, Jul. 1, 2011, pp. 1160-1167, vol. 21, No. 7.

* cited by examiner

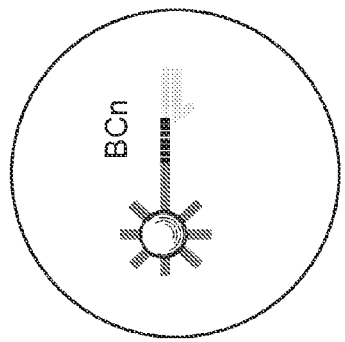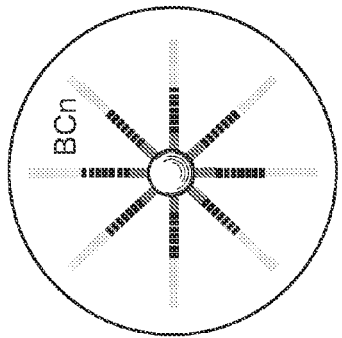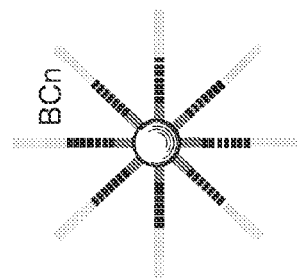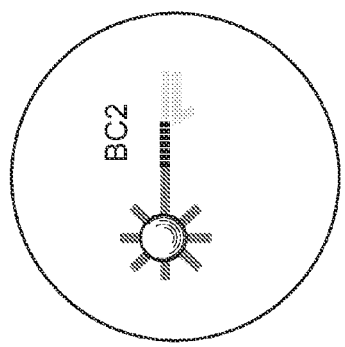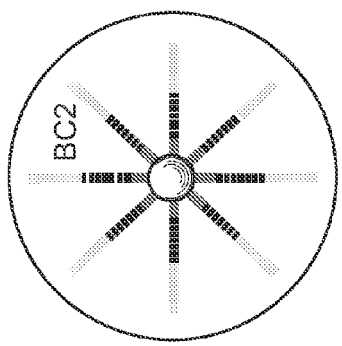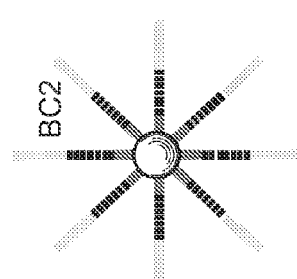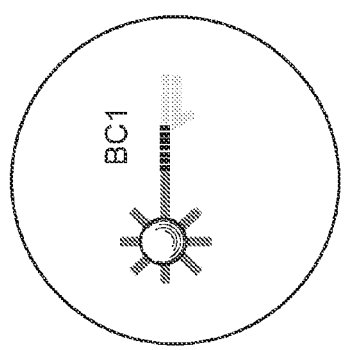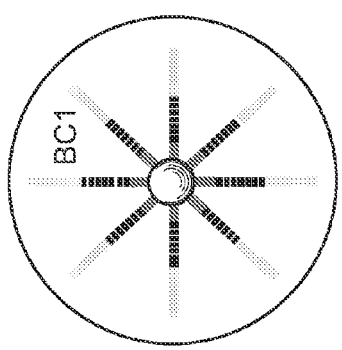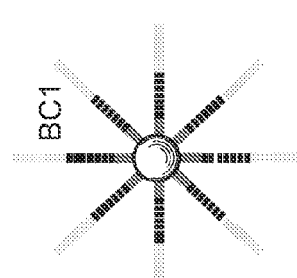
FIG. 1C
FIG. 1D
FIG. 1E

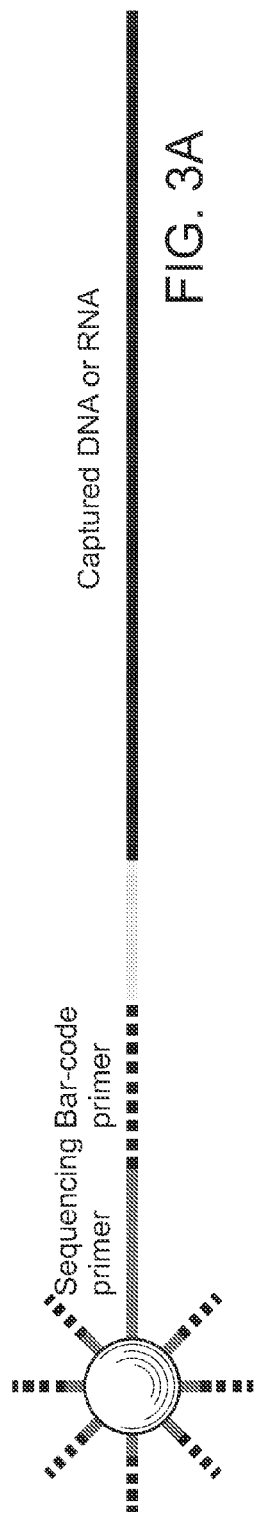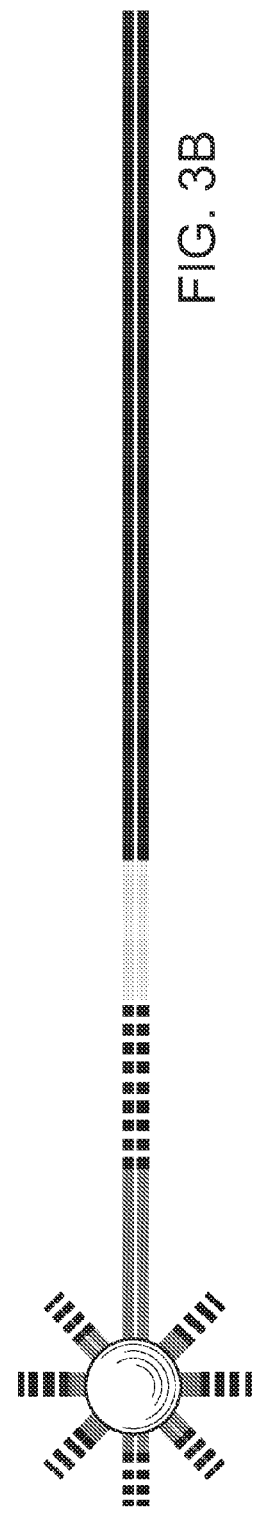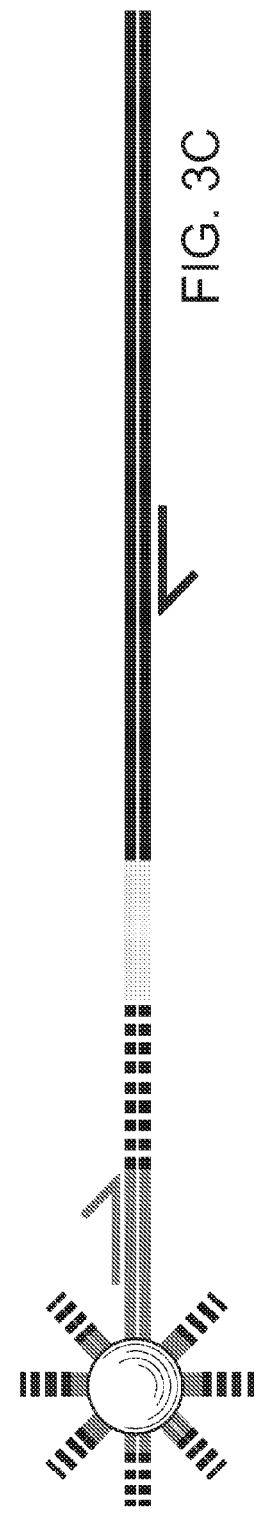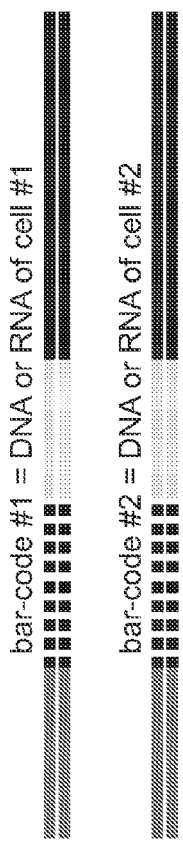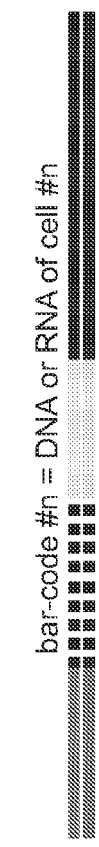

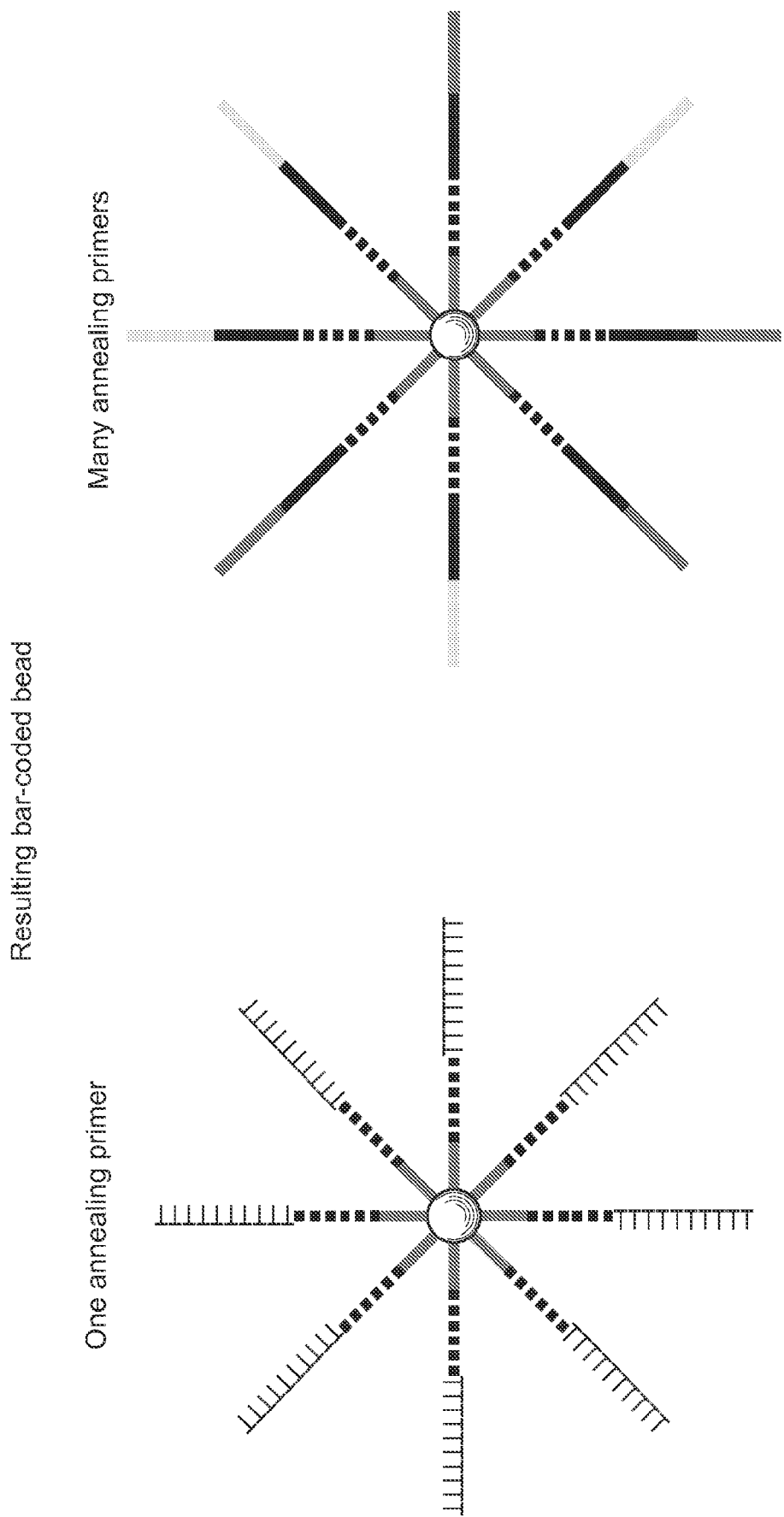

Illumina PE Library:

5' PRIMER    [VE sequencing]
         (Cluster)
5' (AATGATACGGCGACCACCGAGATCT) [ACACTCTTTCCCTACACGACGCTCTTCCGATCT] (N)
                                        (Cluster)
[bar-code sequencing]
[AGATCGGAAGAGCGGTTCAGCAGGAATGCCGAGACCG] (ATCTCGTATGCCGTCTTCTGCTTG) 3'

3' PRIMER    [VE sequencing]
         (Cluster)
3' (TTACTATGCCGCTGGTGGCTCTAGA) [TGTGAGAAAGGGATGTGCTGCCGAGAAGGCTAGA] (N)
                                        (Cluster)
[bar-code sequencing]
[TCTAGCCTTCTCGCCAAGTCGTCCTTACGGCTCTGGC] (TAGAGCATACGGCAGAAGACGAAC) 5'

FIG. 9A single cells transcriptome library

5' PRIMER
   Cluster                            anchor seq primer A                                    Cluster B
5' (AATGATACGGCGACCACCGAGATCT) [ACACTCTTTCCCTACACGACGCTCTTCCGATCT] [---BC(N20)---] CAGC[oligodT]
                                         rev seq primer B
(RNA) [AGATCGGAAGAGCGGTTCAGCAGGAATGCCGAGACCG] (ATCTCGTATGCCGTCTTCTGCTTG) 3'

3' PRIMER
   Cluster                            anchor seq primer A                                    Cluster B
3' (TTACTATGCCGGCTGGTGGCTCTAGA) [TGTGAGAAAGGGATGTGCTGCGAGAAGGCTAGA] [---BC(N20)---] CAGC[oligodT]
                                         rev seq primer B
(RNA) [TCTAGCCTTCTCGCCAAGTCGTCCTTACGGCTCTGGC] (TAGAGCATACGGCAGAAGACGAAC) 5'

FIG. 9B

Sample Bar-code Oligonucleotide

BEad– [ACACTCTTTCCCTACACGACGCTCTTCCGATCT][--BC(N20)--]CAGC[oligodT]

BC=bar-code

FIG. 9C

HIGH-THROUGHPUT SINGLE CELL BARCODING

RELATED APPLICATION DATA

This application is a National Stage Application under 35 U.S.C. 371 of co-pending PCT application PCT/US2011/055803 designating the United States and filed Oct. 11, 2011; which claims the benefit of U.S. Provisional Application No. 61/391,364 and filed Oct. 8, 2010 each of which are hereby incorporated by reference in their entireties.

STATEMENT OF GOVERNMENT INTERESTS

This invention was made with government support under HG003170 awarded by the National Institutes of Health. The Government has certain rights in the invention.

FIELD

The present invention relates to methods and compositions for obtaining and analyzing nucleic acid sequences derived from many single cells at once.

BACKGROUND

Classical single cell analysis is performed by isolating a single cell into a single well of a processing plate from which DNA and/or RNA can be amplified or where the cell can be subculture into a larger population, with both approaches performed until enough genomic material is achieved for subsequent downstream processing. A limitation of such approaches is that it is not always possible to isolate single cells from a tissue section or a complex cellular mixture or population. Furthermore, in a clonally amplified cell population in culture, even if the cells should present the exact same genome, which they should in theory, the transcriptomic information is variable from one cell to another. Also, culturing cells modifies their expression patterns, so it is often preferable to capture the transcriptomic information when the cells are in their original environment. In addition, the extreme low amounts of DNA and/or RNA obtained when isolating a single cell makes downstream processing steps quite challenging. Moreover, the processes by which DNA and/or RNA are amplified to large enough amounts to allow such analysis causes significant bias in the resulting material and, therefore, is not representative of the nucleic acids in the cell. Finally, classical approaches are limited in the amount of single cells that can be assayed in one analysis. For example, a complex population of 10,000 cells is to be studied, 10,000 cells would need to be sorted and separated (using, e.g., approximately 100×96 well plates), which requires substantial investment in costly automation equipment as well as significant processing time and additional costs.

Early approaches included split pooled DNA synthesis. While split pooled DNA synthesis on beads can potentially be used to achieve uniquely bar-coded beads (Brenner et al. (2000) *Proc. Natl. Acad. Sci. USA* 97:1665), the technical difficulties associated with such an approach and the incorporation inefficiency of nucleotide during chemical synthesis of the sequence, results in beads having very few oligonucleotide sequences with correct sequences and/or length. Even when nucleotide synthesis chemistry is quite efficient, there is, on average, 1% non-incorporation at each nucleotide cycle. Consequently, attempts to synthesize a clonal bar-code on beads of proper length split pooled DNA synthesis were unsuccessful. For example, for a typical oligonucleotide of 50-60 nucleotides this error rate would result in less than 40% of the oligos on the beads having the correct sequence. Moreover, because the oligonucleotides are synthesized on a solid support it is impossible to identify the correct one, using purification approaches such as with HPLC purification or PAGE. Split pool synthesis was originally developed by Linx Therapeutics, who was acquired by Solexa who was acquired by Illumina based on the early work on split pool synthesis, but the technology was abandoned because of these issues. Thus, the efficient use of bar-coded beads has not been achieved. Beads with an internal dye gradient core (such as the one used by Luminex Corporation) can be used in application where the overall bead bar-code signal is used. While that approach is acceptable when an average signal intensity is desired, it is inadequate where the downstream use of these molecules requires unique identification of the cell. Also "luminex beads" can only be generated in a limited amount which result in limited capability for probing more then a few hundreds of cells.

The present approach offers particular advantages over earlier approaches such as split pooled DNA synthesis on bead.

SUMMARY

The present approach efficiently produces bar-coded beads coated with clonal copies of the bar-coded oligonucleotides having the correct sequence. Moreover, the speed, ease and cost of production is also advantageous. And, unlike split pooled DNA synthesis on beads, millions of uniquely bar-coded beads can be generated for single cell analysis.

In one aspect, the invention consists of an approach for bar-coding many single cells in a complex mixtures of cells. Each cell is provided with a unique individual bar-code for each cell. The unique bar-code allows each cell's nucleic acids (genome or transcriptome) to be associated with the original cell. Thus, for any given individual cell multiple different genes and transcripts can be identified and correlated to the same cell because the sequences share the same unique bar code.

The unique bar-code is inserted into each individual cell in a way that each cell receives one unique bar-code and is present in a large enough amount to allow subsequent genomic or transcriptomic targeting. Once the bar-code is inserted, downstream manipulations are conducted to capture and then sequence all these unique bar-codes and the genome or transcriptome sequences of interest in one simultaneous reaction. The present approach, when coupled with high-throughput sequencing technology allows analyzing a large number of single cells and achieving the analysis in one single reaction assay. In principle, one can sequence any number of cells and any number of targeted regions per cell. The number of single cells that can be processed is limited only by practical constraints, such as the speed of high throughput sequencing; for example. In some embodiments, high-throughput sequencing technologies are used, such as the ones conducted of sequencing platform such as Illumina HiSeq or genome analyzer, Roche 454, Pacific Bioscience, Ion Torrents, Harvard Polonator, ABI Solid or other similar instruments in the field. Classic sequencing approaches, such as Sanger sequencing can be used; however, the true power in the technology is to be able to sequence a larger number of sequences from single cells simultaneously. High-throughput sequencing platforms are thus better-suited for most embodiments. If a sequencing platform generates 10 million reads per run, then one can sequence one unique transcript across 1 million cells to achieved a 10× coverage. In other embodiments, a partial transcriptome, for example targeting 10,000 unique transcripts, requires only 100 cells to be targeted for capture and sequencing.

In some embodiments, full or targeted transcriptome RNA analysis is performed. Thus, in a single cell, only selected transcripts may be sequenced. In other applications, all or substantially all transcripts may be captured and sequenced. In yet other embodiments, full or partial genomic DNA analysis is performed.

Analyses of multiple cells in heterogeneous cell populations is particularly useful when studying complex samples or mixtures. Complex samples or cell mixtures include, for example, metagenomic samples, normal and cancerous tissue sections, embryonic and stem cell colonies. Genome and transcriptome sequencing is desirable where sequences are highly divergent; for example, in certain cell types or in cells at certain stages. Particularly suitable applications include molecular haplotyping, HLA typing, and T- and B-cell receptor profiling. Metagenomic samples refers to samples containing genomes from multiple origins, such as species. For example, the present approach may be applied to mixtures of bacterial species to allow sequencing of nucleic acids from multiple bacteria in one assay followed by correlating the sequences to the same bacterial cell. Similarly, nucleic acid sequences of foreign cells living in the mouth can be determined and correlated to the same cell.

Further features and advantages of certain embodiments of the present invention will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 1A-1E schematically depict a method of amplifying each unique molecule composed of a degenerate barcode on a bead according to certain aspects of the invention. (A) Attach barcoded template oligonucleotide. (B) saturate solid support with anchor primer. (C) Perform emulsion PCR. (D) Emulsion PCR completed. (E) Barcoded beads are recovered.

FIGS. 3A-3D schematically depict downstream processing of recovered beads bound to barcoded fragments. (A) Example of one RNA template. (B) Second strand synthesis. (C) Gene specific primer, restriction digest or universal adapter ligation. (D) Recovered barcoded DNA, ready for high-throughput sequencing.

FIGS. 6A-6B depicts a method to generate multiple copies of a uniquely degenerate barcode for single cell analysis according to certain aspects of the invention relating to targeting more than one nucleic acid sequence of interest. The left panel in FIGS. 6A and 6B shows an oligo-dT sequence annealing primer, which can target polyA tails of mRNAs found in a cell. The right panel in FIGS. 6A and 6B demonstrates using a "universal sequence" primer, which has a sequence complementary to an overhang common to several annealing primer sequences, to generate a bead having oligonucleotides that anneal to multiple different nucleic acid targets of interest (shown in red and blue at the 3' end of the oligonucleotide.)

(FIG. 7A: 0.1 pM; FIG. 7B: 1 pM, FIG. 7C: 10 pM, and FIG. 7D: 100 pM). FIG. 7E shows the 100 pM sample overlaid with beads. See Example 1.

FIG. 8A shows overlay of uniquely bar-coded beads over white light, showing clonality of beads with an optimal amount of starting template. FIG. 8B shows one cycle sequencing of the bar-code on the fluorescence channels only. FIG. 8C shows white light only. FIG. 8D shows single bead capture in emulsion. FIG. 8E shows bar-coded beads in presence of lysed cells in emulsion post-amplification. FIGS. 8F and G are magnifications of FIG. 8E. FIG. 8H shows introduction of fluorescent bar-codes in single cells FIGS. 9A-9C shows sequences used in aspects of the invention. FIG. 9A shows 5' and 3' sequences of a primer (SEQ ID NO:1) used in the Illumina system. FIG. 9B shows 5' and 3' sequence of a primer (SEQ ID NO:2) used in aspects of the invention, including anchor sequence primer, 20-nucleotide bar-code position (—BC(N20)-), and oligo dT sequence. The cluster sequences facilitate sequencing in the Illumina system. FIG. 9C shows a sample oligonucleotide attached to a bead having an anchor sequence primer, 20-nucleotide bar-code (—BC(N20)-), and oligo dT sequence (SEQ ID NO:3).

DETAILED DESCRIPTION

In certain aspects, the methods and compositions described herein are useful for single cells analysis, such as, e.g., for the study of genomes, transcriptomes, proteomes, metabolic pathways and the like of complex cell samples. In other aspects, the methods and compositions described herein can be used for antibody discovery by pairing heavy and light chain in single B and T cells, as well as for HLA typing, and long range haplotyping. In still other aspects, the methods and compositions described herein can be used to monitor the impact of small molecule and drugs and their effect in complex normal or cancerous samples for the discovery of new drugs. In yet other aspect, the methods and composition can be used to detect and analyze pathogens such as bacteria or viruses in biological samples.

In certain exemplary embodiments, methods are provided for creating clonal copies of barcode sequences (e.g., degenerate barcodes) and delivering the barcode sequences into a plurality of single cells. According to one aspect of the invention, a plurality of unique nucleic acid sequences comprising a degenerate barcode are amplified on a support (e.g., a bead) such that each discrete area of the support (e.g., each bead) will be coated with clonal copy of a starting nucleic acid sequence (FIG. 1). Accordingly, each discrete area of a support; bead, for example, will be uniquely barcoded with a plurality of targeting barcode oligonucleotides. In certain exemplary embodiments, emulsion PCR is performed, wherein degenerate oligonucleotide sequences are attached to a bead using a dilution equivalent maximum of one molecule per bead. The bar-code oligonucleotide length is related to cell sample size of interest. Generally, bar-codes are at least 3 nucleotides long. Often, they are about 20 nucleotides. Thus, for example, a support-attached oligonucleotide having a total length of about 50-60 nucleotides, includes nucleotides encoding a sequencing primer, 20 nucleotides for the bar-code, and an annealing primer.

Figure 1A:
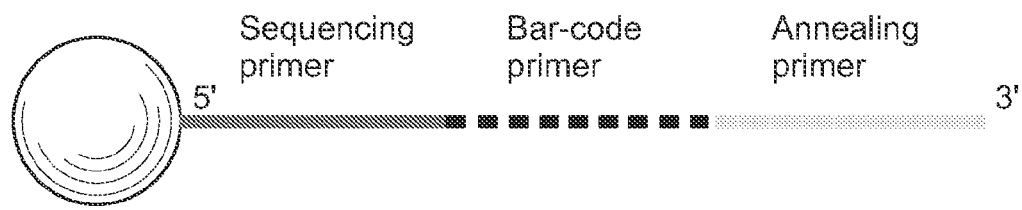

In some embodiments, the support is a bead. The initial template oligonucleotide loaded on the beads has a sequencing primer region (which will be used to facilitate sequencing of the bar-code), a degenerate region (the actual bar-code) and an annealing primer region, which has a sequence complementary to the target nucleic acid sequence or sequences of interest. The annealing primer can be DNA or RNA (FIG. 1A). Some beads may contain oligonucleotides that bind to more than one target nucleic acid of interest.

Figure 1B:

The beads are then saturated with an anchor primer. (FIG. 1B). The anchor primer has the same sequence as the sequencing primer region of the template oligonucleotide. The anchor primer serves as the second PCR priming end, which allows attachment of the product generated during emulsion PCR to the beads. The beads are then amplified in emulsion PCR (FIG. 1C) using a primer complementary to the annealing section of the starting molecule. When emulsion PCR is complete, the anchor primer is extended and contains a copy of the bar-code and the annealing primer. The bead can subsequently be purified from the emulsions and used in downstream applications.

Once the bar-coded beads are prepared, they are used in a second emulsion PCR in the presence of a single cell. The cell is contained within its own unique emulsion, allowing simultaneous PCR in a single assay that contains many cells. (FIG. 2). The beads and cells may be introduced to each other in any suitable way. For example, by transfection using liposomes, or by emulsification. Samples containing multiple beads and multiple cells are diluted to achieve a maximum of one bead and one cell per emulsion PCR reaction. In FIG. 2, an example of one bead-cell event is shown.

In some embodiments, thousands to millions of the events shown in FIG. 2 may be performed in a single assay, such as one assay performed in a single well. Each single cell is sequestered into its own unique emulsion in the presence of one bar-coded beads. The multiple reaction are in the same reaction volume for all the cells. Because so many cells are analyzed in a single assay, the approach is equivalent to mixing millions of wells of PCR plates. Therefore a single assay is not limited in the amount of single cells to target, or the amount of transcript to target per single cells, provided each cell is uniquely bar-coded in either single emulsion per cell or through liposome transfection of a single bead or bar-code system. See FIG. 2A. Millions of emulsions can be present in a single assay; i.e in a single well.

Figure 2A:
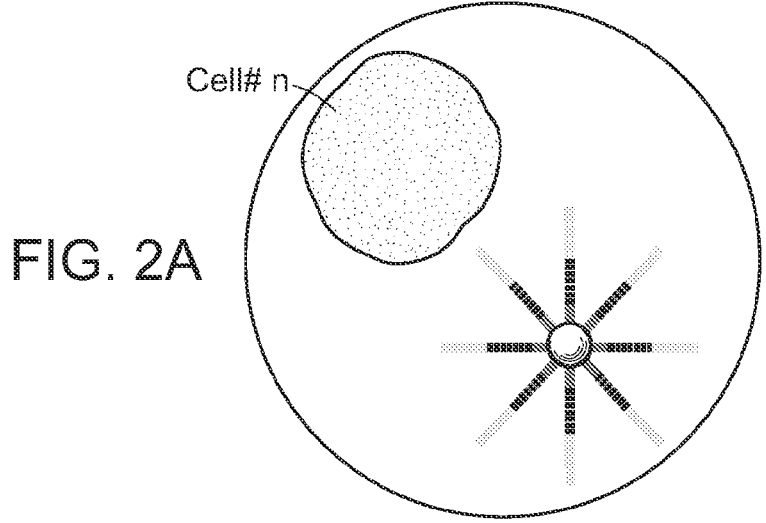
FIGS. 2A-2D schematically depict emulsion PCR of a single cell. (A) Capture of cell and barcoded bead in an emulsion. (B) Lyse cell. (C) Anneal DNA and/or RNA to barcoded bead followed by primer extension and/or reverse transcription.
Figure 2B:
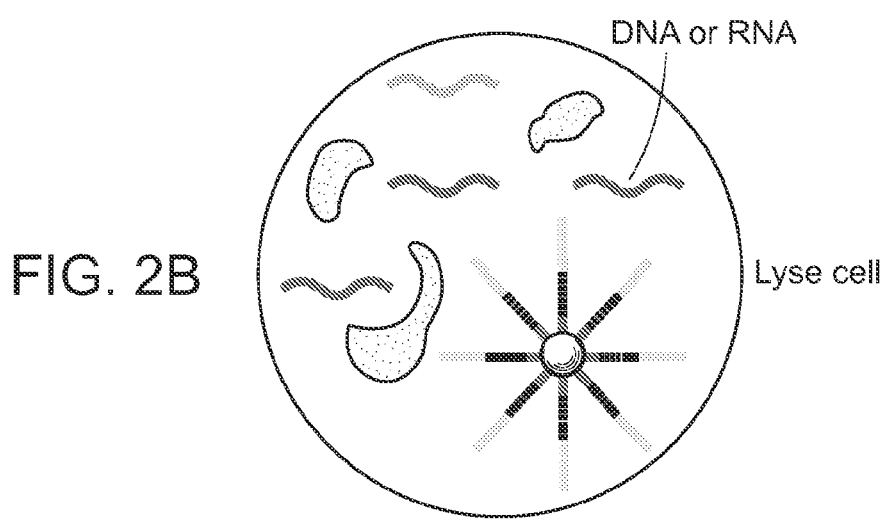
Figure 2C:
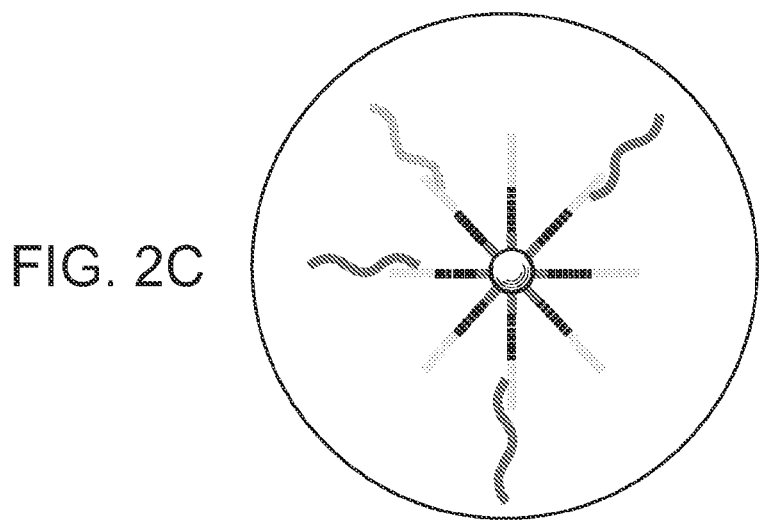
Figure 2D:
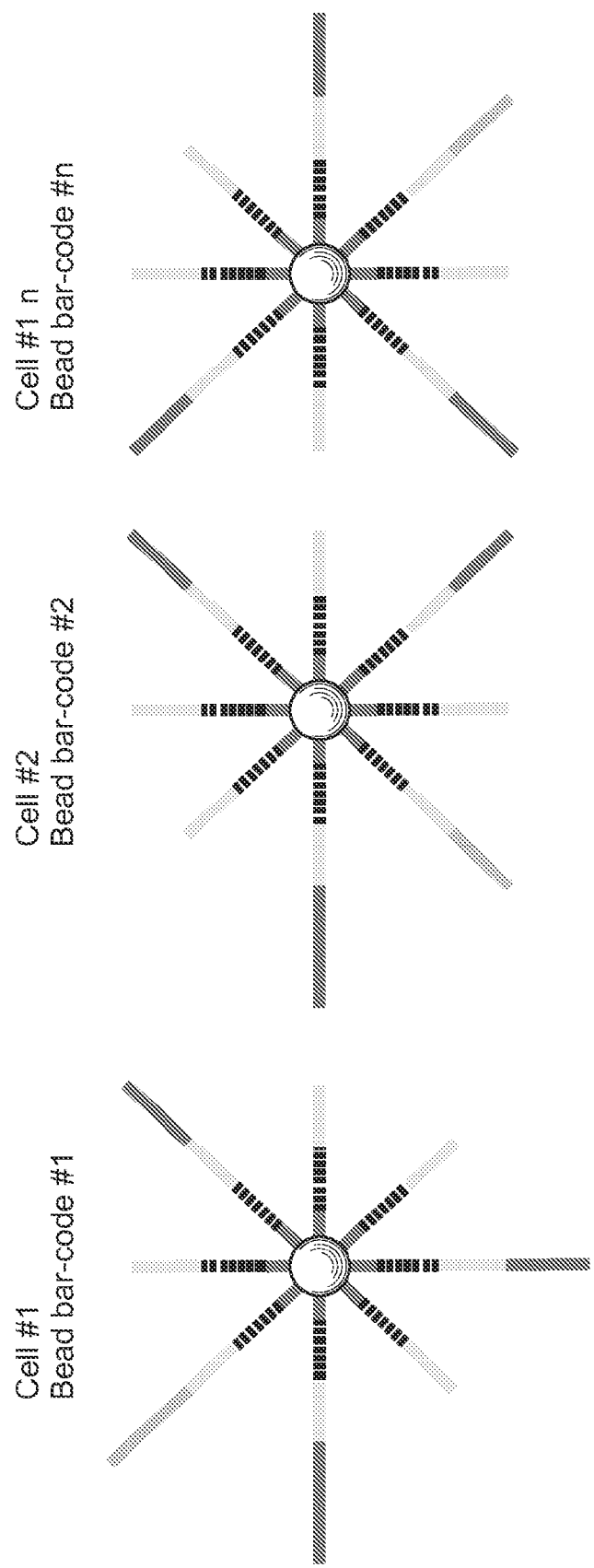

Upon cell lysis, the nucleic acid target of interest is annealed to the complementary sequences on the bar-coded bead template. FIG. 2B. Reverse transcription, for a RNA target, or primer extension, for a DNA target, is performed, and appends a bar-code to the cell RNA or DNA target. FIG. 2D. Within one cell, the same bar-code is added to all the target sequences. Thus, as shown in FIG. 2D, Cell number 1, bead bar code number 1 has captured four examples of the target sequence (green, yellow, purple, and red). Each independent cell in the reaction has a different bar code. FIG. 2D.

DNA from Beads with bar-coded fragments of interest are recovered and processed in downstream assays. When the bead has RNA attached, cDNA synthesis is performed, followed by PCR amplification using gene specific primer (or restriction cleavage, and/or adapter ligation, follow by PCR) similarly to what has been described previously (Kim et al. (2007) *Science* 316:1481). See FIG. 3. Sequencing of DNA using high-throughput technology is then performed. The sequencing primer is used to sequence the bar-code, through the annealing primer into the target sequence. The target sequencing conveys transcript identity and expression levels, or other genomic or transcriptomic sequence of interest. The bar-code sequence allows each target sequence to be correlated to the single cell from which the sequences originated. While each transcript originating from one cell will have the same bar-code sequence, variation in genomic or transcriptomic information across the cell population is determined by assaying many single cells at the same time. Because each single cell contains a unique bar-code different from the other single cells, the identified sequences having the same bar-code can be correlated to the same originating cell.

Figure 6A:
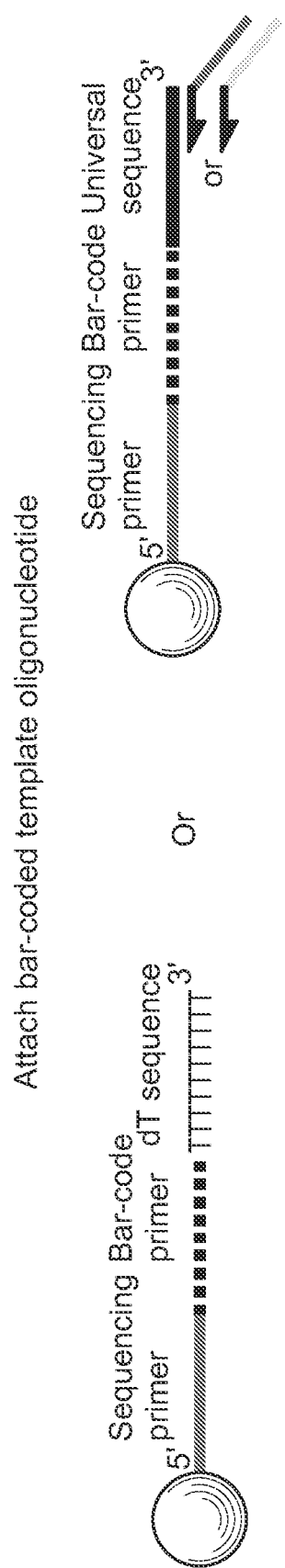
Figure 7B:
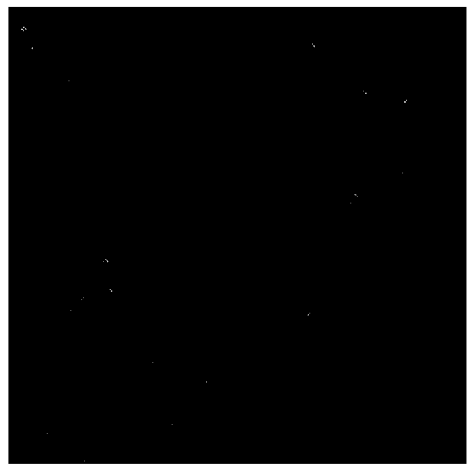
FIGS. 7A-7E show bead clonality using different concentrations of primer.
Figure 7D:
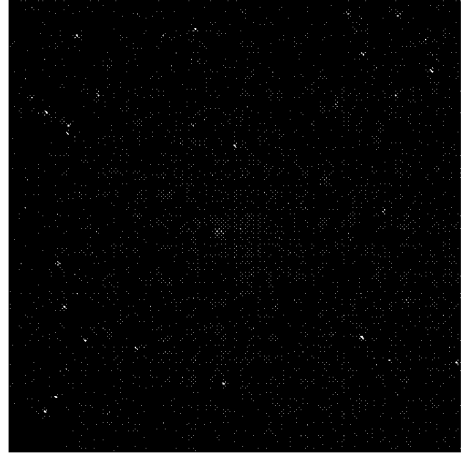
Figure 7A:
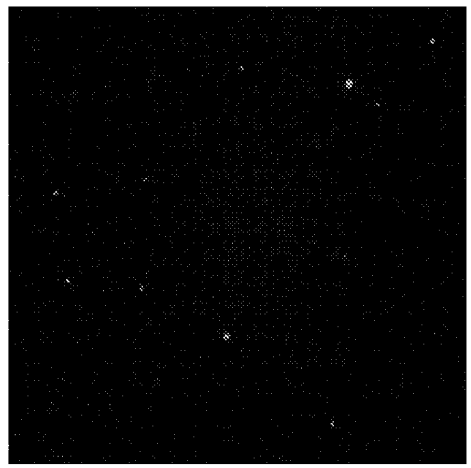
Figure 7C:
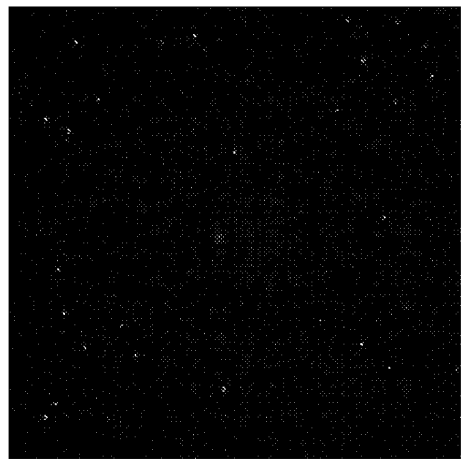
Figure 7E:
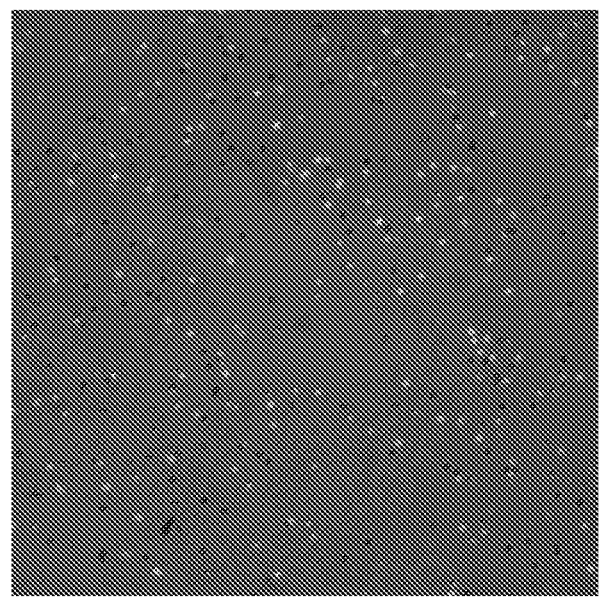
Figure 8B:
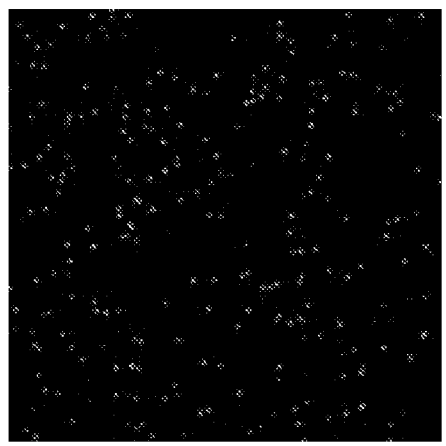
FIGS. 8A-8H shows bead clonality in emulsions.
Figure 8D:
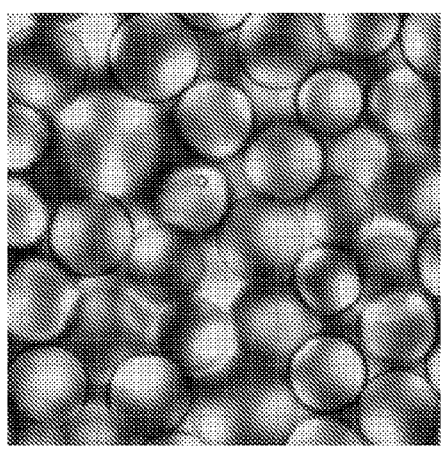
Figure 8A:
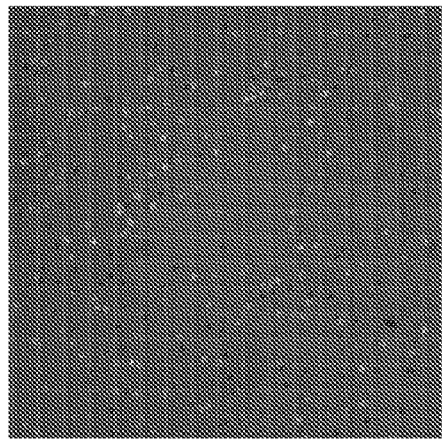
Figure 8C:
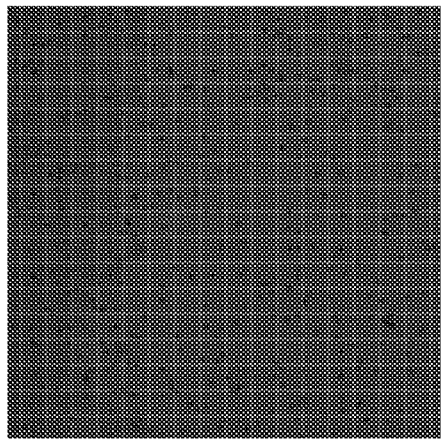
Figure 8F:
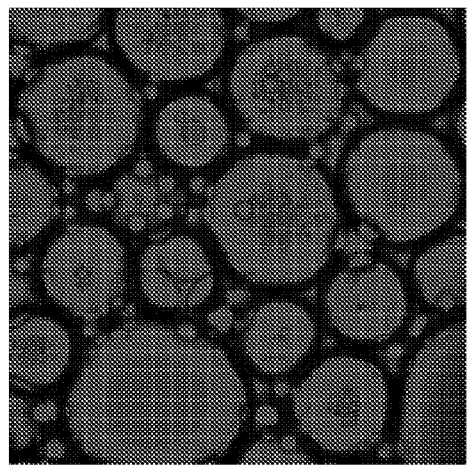
Figure 8H:
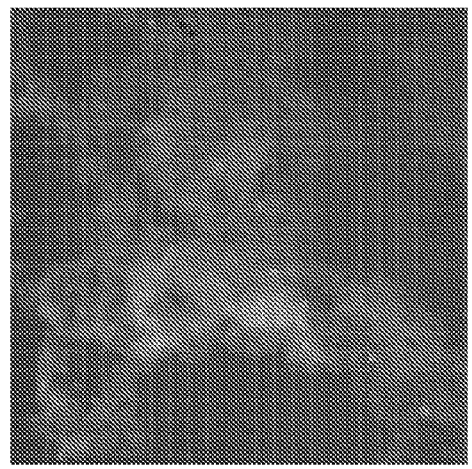
Figure 8E:
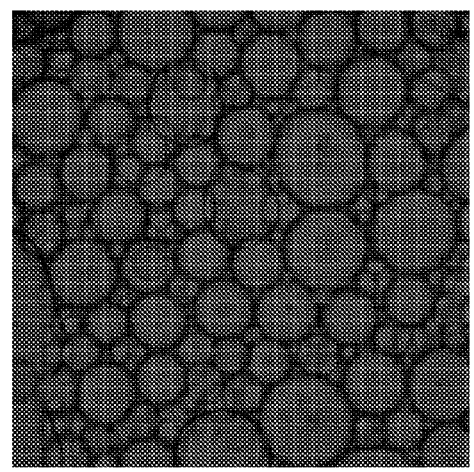
Figure 8G:
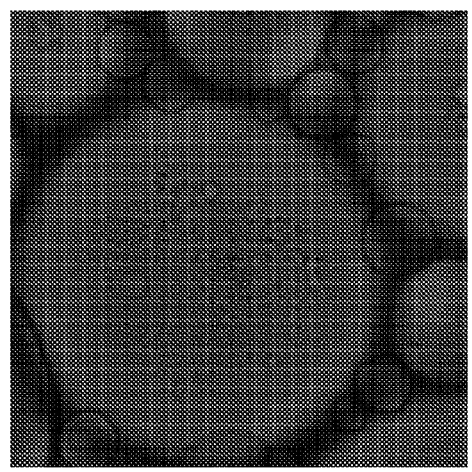

In certain embodiments, multiple mRNAs from each single cell can be obtained and analyzed. For example, oligo-dT (or similar primers) may be used as the annealing primer. See FIGS. 6A and 6B. The oligo-dT sequence anneals to mRNA polyA tails and thus capture simultaneously multiple messenger RNAs from a single cell. This allows for complete or substantially complete transcriptome analysis of multiple single cells in a complex mixture. Characterizing the transcriptomes of multiple cells on a per-cell basis has particular application in studies investigating which cells are malignant than others cancer samples. Moreover, in patients undergoing cancer therapy, the present approach provides for monitoring mutation of each cell's genome and transcriptome before and after treatment; for example with a drug, or following surgery. This information is particularly useful when coupled with medicines known to be affected by the sequence of a protein. For example, the EGFR inhibitor Erbitux® (cetuximab) is ineffective when used with certain mutations of K-ras. The present approach can be used diagnostically to determine, down to the single cell level, how many cells in a tumor sample carry the mutations that make the cells Erbitux® resistant. Information regarding the nucleic acid sequences of multiple proteins in each tumor cell is valuable in determining whether to continue or stop treatment with a given drug or switch to an alternative drug.

In another embodiment, at least two oligonucleotides having different annealing primers are attached to the same bead, which allows several target nucleic acids in the same cell to be captured and sequenced. To produce beads containing different annealing primers a universal sequence is attached downstream of the bar-code primer. See FIGS. 6A and 6B. The universal sequence is complementary to an overhang region on a second primer that contains the annealing primer, which targets the gene of interest. Multiple annealing primers, each targeting a different gene of interest, may be used. The universal sequence, common to the overhangs of all the annealing primers allows incorporation of the multiple annealing primer sequences onto the beads by PCR. See FIGS. 6A and 6B.

Beads with multiple annealing primers targeting different nucleic acids of interest have particular use in immune cell applications. In one embodiment, specific sets of targeting oligonucleotides complementary to the heavy and light chains of the B cell antibody coding gene or its RNA are used to capture the pairing of each unique single cell's heavy and light chains that define each specific antibody. In another embodiment, sequences encoding T cell receptor components may be targeted and sequenced. See (Embleton et al. (1992) *Nucleic Acids Res.* 20(15):3831; Chapal et al. (1997) *Biotechniques* 23(3):518).

In yet other embodiments, annealing primers are selected for analyzing small nucleotide polymorphisms (SNPs), and for long range haplotyping (Zhang et al., "Long-range polony haplotyping of individual human chromosome molecules," Nat Genet. 2006 March; 38(3):382-7). These approaches provide specific information for each cell in multiple-cell biological samples.

In certain immune related examples, bar-coding is not necessary if one uses strategies to attach the heavy and light chain prior to PCR or cleavage of the molecules from the beads, such as ligation, of CRE-LOX coupling or fragments of each unique bead, as described by Embleton et al. (1992) *Nucleic Acids Res.* 20(15):3831; Chapal et al. (1997) *Biotechniques* 23(3):518, but in such way that many single cell at once can be treated as described in the current invention.

As used herein, the term "barcode" refers to a unique oligonucleotide sequence that allows a corresponding nucleic acid base and/or nucleic acid sequence to be identified. In certain aspects, the nucleic acid base and/or nucleic acid sequence is located at a specific position on a larger polynucleotide sequence (e.g., a polynucleotide covalently attached to a bead). In certain embodiments, barcodes can each have a length within a range of from 4 to 36 nucleotides, or from 6 to 30 nucleotides, or from 8 to 20 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) *Science* 285:901; Brenner (2000) *Genome Biol.* 1:1 Kumar et al. (2001) *Nature Rev.* 2:302; Giaever et al. (2004) *Proc. Natl. Acad. Sci. USA* 101:793; Eason et al. (2004) *Proc. Natl. Acad. Sci. USA* 101—:11046; and Brenner (2004) *Genome Biol.* 5:240.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T/U, or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, at least about 75%, or at least about 90% complementary. See Kanehisa (1984) *Nucl. Acids Res.* 12:203.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Nucleoside" as used herein includes the natural nucleosides, including 2'-deoxy and 2'-hydroxyl forms, e.g. as described in Komberg and Baker, *DNA Replication,* 2nd Ed. (Freeman, San Francisco, 1992). "Analogs" in reference to nucleosides includes synthetic nucleosides having modified base moieties and/or modified sugar moieties, e.g., described by Scheit, *Nucleotide Analogs* (John Wiley, New York, 1980); Uhlman and Peyman, *Chemical Reviews,* 90:543-584

(1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents*, 6: 855-870 (1996); Mesmaeker et al., *Current Opinion in Structural Biology*, 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

As used herein, the terms "nucleic acid molecule," "nucleic acid sequence," "nucleic acid fragment," "oligonucleotide," "oligonucleotide fragment" and "polynucleotide" are used interchangeably and are intended to include, but are not limited to, a polymeric form of nucleotides that may have various lengths, either deoxyribonucleotides or ribonucleotides, or analogs thereof. Nucleic acid molecules include single stranded DNA (ssDNA), double stranded DNA (dsDNA), single stranded RNA (ssRNA) and double stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In certain exemplary embodiments, large polynucleotides are provided. In certain aspects, isolation techniques that maximize the lengths of polynucleotides (e.g., DNA molecules) obtained are used. For example, in situ lysis or deproteinization (e.g., with EDTA, detergent, protease, any combinations thereof and the like) after agarose embedding (as routinely performed for pulsed field gel electrophoresis) can be used to obtain polynucleotides.

Nucleic acid molecules may be isolated from natural sources or purchased from commercial sources. Oligonucleotide sequences may also be prepared by any suitable method, e.g., standard phosphoramidite methods such as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos.

5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

Nucleic acid molecules may be obtained from one or more biological samples. As used herein, a "biological sample" may be a single cell or many cells. A biological sample may comprise a single cell type or a combination of two or more cell types. A biological sample further includes a collection of cells that perform a similar function such as those found, for example, in a tissue. Accordingly, certain aspects of the invention are directed to biological samples containing one or more tissues. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g. erythrocytes, granulocytes, neutrophils, eosinophils, basophils, monocytes, T-lymphocytes (also known as T-cells), B-lymphocytes (also known as B-cells), plasma cells, megakaryocytes and the like), neurons, germ cells (e.g., spermatozoa, oocytes), amniotic fluid cells, placenta, stem cells and the like. A tissue sample includes microscopic samples as well as macroscopic samples. In certain aspects, a sample can be obtained from one or more of single cells in culture, metagenomic samples, embryonic stem cells, induced pluripotent stem cells, cancer samples, tissue sections, biopsies and the like, and any combinations of these.

In certain aspects, nucleic acid sequences derived or obtained from one or more organisms are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, $2^{nd}$ Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, $2^{nd}$ Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

In certain exemplary embodiments, oligonucleotide sequences are immobilized on a solid support. The support can be simple square grids, checkerboard (e.g., offset) grids, hexagonal arrays and the like. Suitable supports include, but are not limited to, slides, beads, chips, particles, strands, gels, sheets, tubing, spheres, containers, capillaries, pads, slices, films, culture dishes, plates (e.g., 96-well, 48-well, 24-well, 12-well, eight-well, six-well, four-well, single-well and the like), cell surfaces (e.g., *S. aureus* cells) and the like. In various embodiments, a solid support may be biological, non-biological, organic, inorganic, or any combination thereof.

In certain exemplary embodiments, beads and bead-based arrays are provided. As used herein, the term "bead" refers to a discrete particle that may be spherical (e.g., microspheres) or have an irregular shape. Beads may be as small as approximately 0.1 µm in diameter or as large approximately several millimeters in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In accordance with certain examples, a support (e.g., a bead) may have functional groups attached to its surface which can be used to bind one or more reagents described herein to the bead. One or more reagents can be attached to a support (e.g., a bead) by hybridization, covalent attachment, magnetic attachment, affinity attachment and the like. Beads coated with a variety of attachments are commercially available (Dynabeads, Invitrogen). Supports (e.g., beads) may also be functionalized using, for example, solid-phase chemistries known in the art (see, e.g., U.S. Pat. No. 5,919,523).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research,* 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.,* 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques,* 26:112-126 (1999); Becker-Andre et al., *Nucleic Acids Research,* 17:9437-9447 (1989); Zimmerman et al., *Biotechniques,* 21:268-279 (1996); Diviacco et al., *Gene,* 122:3013-3020 (1992); Becker-Andre et al., *Nucleic Acids Research,* 17:9437-9446 (1989); and the like.

In certain exemplary embodiments, methods of determining the sequence identities of nucleic acid sequences are provided. Determination of the sequence of a nucleic acid sequence of interest (e.g., immune cell nucleic acid sequences) can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, ABI-SOLiD, ION Torrents, Complete Genomics, Pacific Bioscience, Helicos, Polonator platforms (Worldwide Web Site: Polonator.org), and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

In certain exemplary embodiments, methods of prognosing, diagnosing and/or monitoring one or more disorders or diseases associated with an infectious agent are provided. Infectious agents include, but are not limited to, viruses, bacteria, fungi, parasites, infectious proteins and the like.

Viruses include, but are not limited to, DNA or RNA animal viruses. As used herein, RNA viruses include, but are not limited to, virus families such as Picornaviridae (e.g., polioviruses), Reoviridae (e.g., rotaviruses), Togaviridae (e.g., encephalitis viruses, yellow fever virus, rubella virus), Orthomyxoviridae (e.g., influenza viruses), Paramyxoviridae (e.g., respiratory syncytial virus, measles virus, mumps virus, parainfluenza virus), Rhabdoviridae (e.g., rabies virus), Coronaviridae, Bunyaviridae, Flaviviridae, Filoviridae, Arenaviridae, Bunyaviridae and Retroviridae (e.g., human T cell lymphotropic viruses (HTLV), human immunodeficiency viruses (HIV)). As used herein, DNA viruses include, but are not limited to, virus families such as Papovaviridae (e.g., papilloma viruses), Adenoviridae (e.g., adenovirus), Herpesviridae (e.g., herpes simplex viruses), and Poxviridae (e.g., variola viruses).

Bacteria include, but are not limited to, gram positive bacteria, gram negative bacteria, acid-fast bacteria and the like.

As used herein, gram positive bacteria include, but are not limited to, *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like.

As used herein, gram negative bacteria include, but are not limited to, *Afipia felis, Bacteriodes, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like.

As used herein, acid-fast bacteria include, but are not limited to, *Myobacterium avium, Myobacterium leprae, Myobacterium tuberculosis* and the like.

As used herein, other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

As used herein, fungi include, but are not limited to, *Aspergilli, Candidae, Candida albicans, Coccidioides immitis, Cryptococci,* and combinations thereof.

As used herein, parasitic microbes include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae,* trapezoidal amoeba and the like.

As used herein, parasites include worms (e.g., helminthes), particularly parasitic worms including, but not limited to, Nematoda (roundworms, e.g., whipworms, hookworms, pinworms, ascarids, filarids and the like), Cestoda (e.g., tapeworms)

As used herein, infectious proteins include prions. Disorders caused by prions include, but are not limited to, human disorders such as Creutzfeldt-Jakob disease (CJD) (including, e.g., iatrogenic Creutzfeldt-Jakob disease (iCJD), variant Creutzfeldt-Jakob disease (vCJD), familial Creutzfeldt-Jakob disease (fCJD), and sporadic Creutzfeldt-Jakob disease (sCJD)), Gerstmann-Sträussler-Scheinker syndrome (GSS), fatal familial insomnia (fFI), sporadic fatal insomnia (sFI), kuru, and the like, as well as disorders in animals such as scrapie (sheep and goats), bovine spongiform encephalopathy (BSE) (cattle), transmissible mink encephalopathy (TME) (mink), chronic wasting disease (CWD) (elk, mule deer), feline spongiform encephalopathy (cats), exotic ungulate encephalopathy (EUE) (nyala, oryx, greater kudu), spongiform encephalopathy of the ostrich and the like.

In certain exemplary embodiments, methods of prognosing, diagnosing and/or monitoring one or more cellular proliferative disorders are provided. Cellular proliferative disorders are intended to include disorders associated with rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal. Id. Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the induction, onset, establishment or growth of neoplasms in a subject or a reduction in the growth of pre-existing neoplasms in a subject. The language also can describe inhibition of the invasion of neoplastic cells into neighboring tissues or the metastasis of a neoplasm from one site to another. Examples of the types of neoplasms intended to be encompassed by the present invention include, but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Cellular proliferative disorders can further include disorders associated with hyperproliferation of vascular smooth muscle cells such as proliferative cardiovascular disorders, e.g., atherosclerosis and restenosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

In certain exemplary embodiments, methods of prognosing, diagnosing and/or monitoring one or more autoimmune disorders are provided. As used herein, the term "autoimmune disorder" is a disease or disorder caused by a subject producing an inappropriate immune response against its own tissues. As used herein, an autoimmune disorder includes, but is not limited to, disorders such as Addison's disease, alopecia areata, ankylosing spondylitis, antiphospholipid sundrome, autoimmune hemolytic anemia, autoimmune hepatitis, autoimmune inner ear disease (AIED), autoimmune lymphoproliferative syndrome (ALPS), autoimmune thrombocytopenic purpura (ATP), Balo disease, Bechet disease, bullous pemphigoid, cardiomyopathy, celiac sprue-dermatitis herpetiformis, chronic fatigue immune dysfunction syndrome (CFIDS), chronic inflammatory demyelinating polyneuropathy, cicatricial pemphigoid, cold agglutinin disease, CREST syndrome, Crohn's disease, Degos disease, dermatomyositis, dermatomyositis-juvenile, discoid lupus, essential mixed cryoglobulinemia, fibromyalgia-fibromyositis, Graves disease, Guillain-Barré, Hashimoto thyroiditis, idiopathic pulmonary fibrosis, idiopathic thrombocytopenia purpura (ITP), IgA nephropathy, insulin-dependent diabetes, juvenile arthritis, lichen planus, lupus, Ménière disease, mixed connective tissue disease, multiple sclerosis, myasthemia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud phenomenon, Reiter syndrome, rheumatic fever, rheumatoid arthritis, sarcoidosis, scleroderma, Sjögren syndrome, stiff-person syndrome, Takayasu arthritis, temporal arteritis/giant cell arteritis, ulcerative colitis, vasculitis, vitiligo, Wegener granulomatosis and the like (See the American Autoimmune Related Diseases Association, Inc. website: aarda.org).

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

EXAMPLE 1

Preparing Bar-Coded Beads a. Loading the Template Bar-Code Oligonucleotide onto Beads Beads (1 μM; C1 carboxylic 1 micron beads) were resuspended by vortexing and transferred in a volume of 80 μl to a 1.5 ml silicon tube (Ambion). The beads were washed twice with 2× (Bind and Wash Buffer contains 10 mM Tris-HCl ph7.5, 1 mM EDTA, 2M NaCl; "B&W"). Beads were isolated using magnets between washes. Nucleotide sequences are listed in Table 4. The washed beads were resuspended in 100 μl B&W to which oligo dT bar-code template oligonucleotide (HSCT_BC_anchor1) were added at the concentrations as shown in Table 1.

TABLE 1

| Tube | Primer Stock Concentration | Primer volume (μl) |
|---|---|---|
| 1 | 100 pM | 80 |
| 2 | 10 pM | 80 |
| 3 | 1 pM | 80 |
| 4 | 0.1 pN | 80 |

The template oligonucleotide and beads were incubated on a rotator for 20 minutes, then washed twice with 200 μl of 1× B&W then resuspended in 100 μl of 2× B&W.

b. Saturating the Beads with Anchor Primer

The beads, pre-loaded with the template oligonucleotide as in Example 1(a) above, were incubated on a rotator for 20 minutes with Anchor primer mix (1 mM HSCT_Bead_anchor1 and 1× B&W buffer) to coat the beads with the anchor primer then washed twice with 200 μl of 1× B&W, once in 200 μl of TE, then resuspended in 100 μl of TE. The anchor primer has a 5' biotin which binds to the streptavidin coated beads. Typically, 30% of the beads have an oligonucleotide. On those beads 100% or substantially all of the anchor primers are typically extended.

c. Emulsion PCR to Synthesis the Oligonucleotide from the Anchor Primer

Aqueous Mix and Oil Mix were prepared as described in Table 2.

TABLE 2

| Component | Volume for 1 tube (μl) | Volume for 4.5 tubes (μl) |
|---|---|---|
| AQUEOUS MIX | | |
| 10 × PCR buffer (Enymatics) | 96 | 432 |
| 50 mM MgCl₂ | 242 | 1089 |
| 25 mM dNTP mix | 135 | 607 |
| 2 mM HSCT_dA-rev_emulsion primer | 6 | 27 |
| OIL MIX | | |
| Tegosoft DEC | 4.4 | 19.8 |
| Mineral oil | 1.2 | 5.4 |
| ABIL WE09 | 425 | 1.9 |

Both solutions are mixed by vortexing. The oil mix is allowed to degass then 5.5 ml portions were placed in 50 ml Teflon-coated aluminum test tubes.

The emulsions were made by adding 800 μl PCR mix, 100 μl Enzymatics Taq (5 U/μl), quickly vortexing and spinning, then immediately adding 60 ml of bar-code anchored beads, followed by vortex and spinning. The 960 ml mix was transferred to a tube of oil and vortexed for 2.25 min at 2200 rpm, which was followed by emulsion PCR using the following PCR protocol steps:

a. 94° C. for 5 min b. 94° C. for 15 sec c. 58° C. for 30 sec d. 70° C. for 75 sec e. Cycle to step b 119 times f. 72° C. for 2 min g. Incubate at ~10° C. until ready to use.

Formation of an emulsion was confirmed by verifying under a microscope that a creamy white consistency was obtained when an emulsifier/oil mixture (240 μl emulsifier: 960 μl oil, or 480 μl emulsifier: 720 μl oil) was added to an aqueous layer (384 μl) and vortexed at 4° C. for 5 minutes. Results are show in FIGS. 7A-7E.

In a similar experiment, Dynal M270 3-micron beads were used under similar conditions and similar results were achieved.

Bar-coding was also achieved as follows.

TABLE 3

| Component | Final concentration | Volume per tube (μl) |
|---|---|---|
| AQUEOUS MIX | | |
| dH20 | — | 520.4 |
| 10 × PCR buffer (Enymatics) | 1× | 80 |
| 25 mM dNTP mix | 2 mM | 64 |

TABLE 3-continued

| | | |
|---|---|---|
| 2 mM HSCT_dA-rev_emulsion primer | 10 µM | 4 |
| 30% (w/v) BSA (Sigma) | 0.06 | 1.6 |

| OIL MIX | | |
|---|---|---|
| Component | Volume for 1 tube (µl) | Volume for 4.5 tubes (µl) |
| Tegosoft DEC | 4.4 | 19.8 |
| Mineral oil | 1.2 | 5.4 |
| ABIL WE09 | 425 | 1.9 |

The aqueous mix was vortexed, then 0.6 ml of mix was added per 1.5 ml tube (Ambion; non-stick). 50 µl of M280 HSCT Anchor bead was added per tube, then the tubes were sonicated for 3 cycles of 10 seconds. After sonication, the tubes were placed on ice, and 80 µl of Taq Polymerase (5 U/µl) was added per tube. The tubes were again vortexed and placed on ice. 800 µl of the mixture was added to the oil phase, the tubes were vortexed and PCR was performed as described in Example 1 part c. In similar experiments 96 well/plates were used. Each well contained 55 µl/well of the mixture.

| Sequence Name | SEQ ID NO: | Sequence |
|---|---|---|
| HSCT_BC_anchor1 | 4 | /52-Bio/ACA CTC TTT CCC TAC ACG ACG CTC TTC CGA TCT NNN NNN NNN NNN NNN NNN NNC AGC TTT TTT TTT TTT TTT TTT TTT TTT T |
| HSCT_Bead_anchor 1 | 5 | /52-Bio/ACA CTC TTT CCC TAC ACG ACG CTC TTC CGA TCT |
| HSCT_clonaltest_B C_seq | 6 | /5Phos/AGA TCG GAA GAG CGT CGT GTA |
| HSCT_dA_rev_emul sion primer | 7 | AAA AAA AAA AAA AAA AAA AAA AAA ACG AC |
| HSCT_BC_anchor_r ev(no-bio) | 8 | AAA AAA AAA AAA AAA AAA AAA AAA AGC TGN NNN NNN NNN NNN NNN NNN NAG ATC GGA AGA GCG TCG TGT AGG GAA AGA GTG T |
| Bead attached to Bar-coded Oligonucleotide | 9 | BEAD/52-Bio/ACACTCTTTCCCTACACGACGCTCTTCCGATCT NNN NNN NNN NNN NNN NNN NNC AGC TTT TTT TTT TTT TTT TTT TTT TTT T ATGTGCTGCGAGAAGGCTAGA/5Phos/ |

Table 4 shows the sequences used in Example 1.

The final sequence attached to the bead in Example 1 is shown in SEQ ID NO:9. The bead is connected 5' to 3' to the oligonucleotide which encodes the anchor primer sequence, the bar code (N20) and an oligo dT primer.

EXAMPLE 5

Introduction of One Unique Bar-Coded Bead Per Cell

Figure 4:
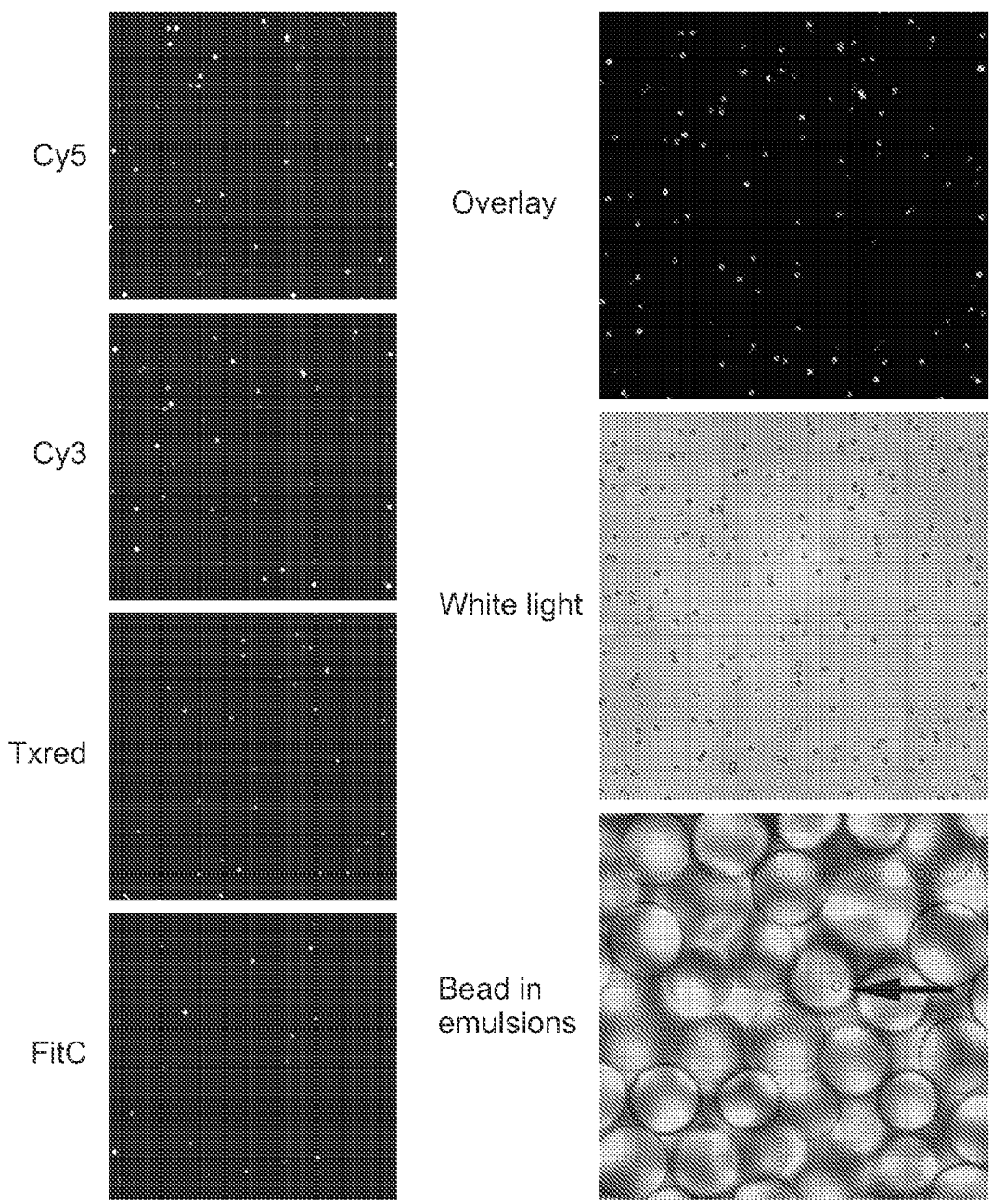
FIG. 4 depicts beads according to certain aspects of the invention. Cy 5 shows presence of an adenine nucleotide at position one of the bar-code. Cy3 the shows presence of a thymine nucleotide at position one of the bar-code Texas Red (TxRed) shows the presence of a cytosine nucleotide at position one of the bar-code. Fluorescein isothiocyanate (FITC) shows the presence of a guanine at position one of the bar-code. Sequentially sequencing each position of the bar-code provides the unique bar-code identifier. Each transcript captured by the beads can be correlated to a unique starting cell because each cell is represented by a unique bar-code.
Figure 5A:
FIGS. 5A-5G depicts a method to generate multiple copies of a uniquely degenerate barcode for single cell analysis according to certain aspects of the invention. (A) Reverse DNA (i.e., starting) template. (B) Circularizing by ligation. (C) Rolling circle amplification using strand displacing polymerase and complementary primer. (D) Inserting into liposome or emulsion with restriction complementary sequence and restriction enzyme. (E) Resulting barcoded oligonucleotides. Each liposome or emulsion contains a unique, degenerate barcode. (F) Each liposome can be fused directly with a single cell (or each barcoded emulsion can be fused with one cell in emulsion). (G) Sequencing query of the barcode region of rolling circle amplification (Rolony) demonstrated clonality. Rolonies were ordered on a grid of 250 nanometer size features.
Figure 5B:
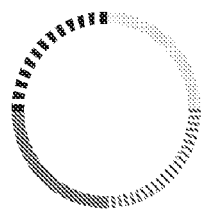
Figure 5C:
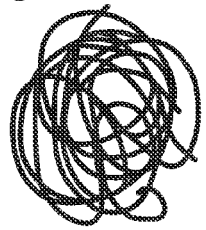
Figure 5D:
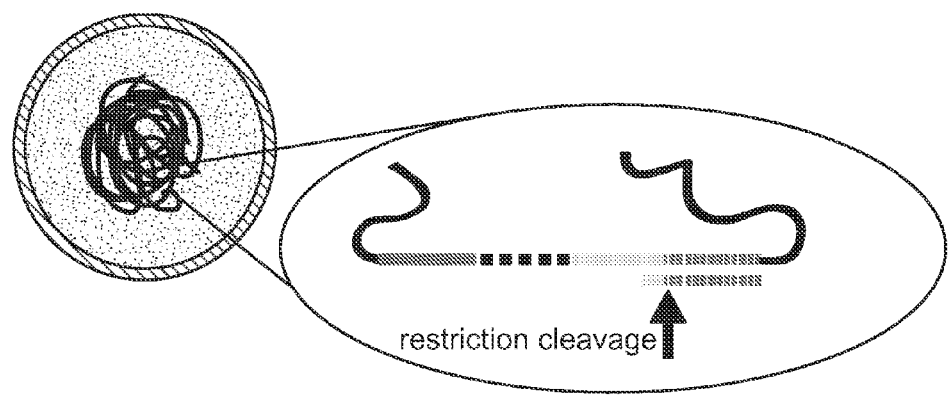
Figure 5E:
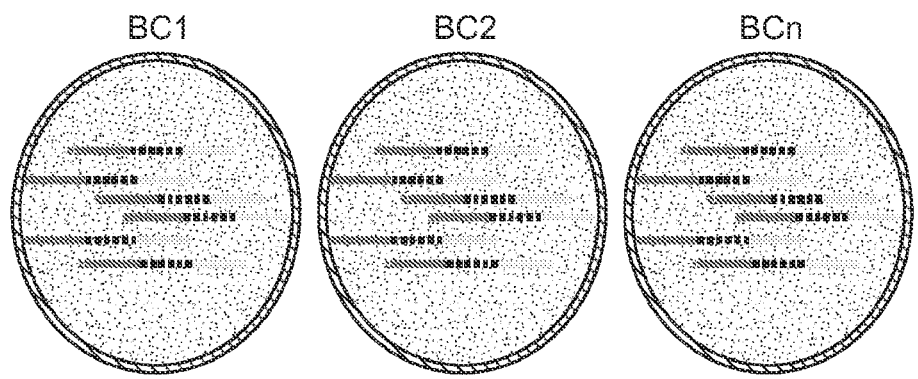
Figure 5F:
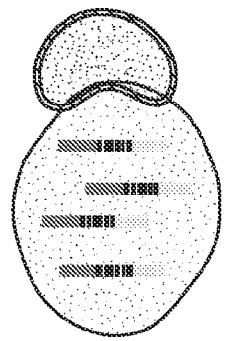
Figure 5G:
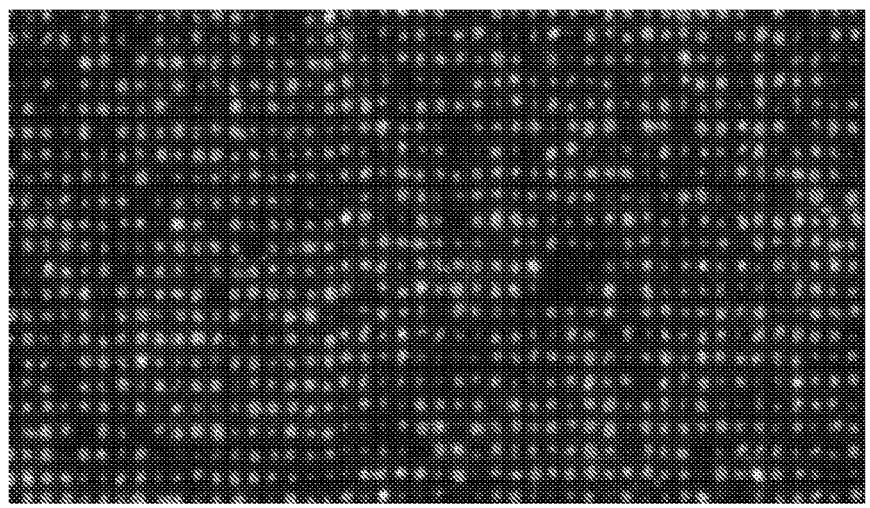

FIG. 4 demonstrates introduction of beads carrying unique bar-coded oligonucleotides into individual cells. Here, beads post-emulsion PCR are sequenced for one base of their bar-code to show that each beads have a unique bar-code and demonstrate clonality. Each nucleotide is queried by a different fluorophores as describe previously (Porreca et al. (2006) Curr. Protoc. Mol. Biol. Chapter 7:Unit 78). Cy 5 shows presence of an adenine nucleotide at position one of the bar-code. Cy3 the shows presence of a thymine nucleotide at position one of the bar-code Texas Red (Txred) shows the presence of a cytosine nucleotide at position one of the bar-code. Fluorescein isothiocyanate (FITC) shows the presence of a guanine at position one of the bar-code. The image overlay of all four fluorophores for a single position on the bar-codes is shown and demonstrates clonality. Clonality refers to each single bead harboring one unique bar-code, which has been successfully amplified onto the bead. If the beads had contained multiple bar-codes; that is, had been non-clonal (for example, having multiple bar-code templates loaded on the bead by accident), the overlay would have demonstrated more than one fluorophore color per bead when querying a single position on the bar-code during sequencing. Complete sequencing of the bar-code, which allows correlation to the cell, is by multiple successive round of sequencing for each nucleotide position.

White light microscopy analysis of the beads and emulsion reaction shows that the starting template and the bead in emulsion were correctly diluted to achieve a maximum of one bead or less per emulsion and one template or less per bead.

EXAMPLE 6

Introduction of Unique Bar-Coded Oligonucleotides on a Grid Support

Multiple copies of the same unique bar-code for single cell analysis were made by rolling circle amplification (RCA) product (Rolony) from a circularized starting bar-code unique oligonucleotide (FIG. 5). See U.S. Published Application No. 20090018024. The uniquely bar-coded Rolony is cleaved into targeting bar-coded oligonucleotides when incubated in presence of a complementary restriction compatible DNA fragment and restriction enzyme. Cleavage may also be performed for example, in liposomes or inside emulsions. Liposomes containing bar-coded oligonucleotides were then fused to cells, allowing the annealing primer to anneal to the target nucleic acid of interest in each cell, as described in the bead-based approach. FIG. 5 shows the query of the Rolony (similar to the query of the bar-coded beads, but ordered on a grid) to demonstrate efficiency at generating uniquely bar-coded clonal Rolony. FIG. 5 demonstrates the rolony are clonally amplified, because for each query of a single position only one fluorophore overlays for that position. Subsequent sequencing of the other nucleotide positions can be performed to identify the complete bar-codes (used to correlated to the single originating cell) and to identify the captured transcripts.

What is claimed is:

1. An oil and water emulsion comprising a single cell sequestered with one bead, wherein the one bead comprises a first polynucleotide attached thereto, wherein the polynucleotide comprises a sequencing primer region, a barcode, and a universal primer region, wherein the sequencing primer region is for sequencing the polynucleotide and wherein the oil and water emulsion further comprises a second polynucleotide, wherein the second polynucleotide comprises a sequence complementary to the universal primer region and an annealing primer region.

2. The oil and water emulsion of claim 1 wherein the one bead further comprises a plurality of first polynucleotides attached thereto wherein each first polynucleotide of the plurality of polynucleotides includes a sequencing primer region, a barcode, and a universal primer region, wherein the sequencing primer region is for sequencing the polynucleotide.

3. The oil and water emulsion of claim 2 wherein the barcode of each polynucleotide is a same barcode sequence.

4. The oil and water emulsion of claim 1 wherein the barcode is unique to the cell.

5. The oil and water emulsion of claim 2 wherein the barcode is unique to the cell.

6. The oil and water emulsion of claim 1 wherein the single cell is a lysed single cell.

7. The oil and water emulsion of claim 1 wherein the single cell is a lysed single cell and a target nucleic acid is annealed to the annealing primer region.

8. The oil and water emulsion of claim 2 wherein the single cell is a lysed single cell and a plurality of target nucleic acids are annealed to first annealing primer regions.

9. The oil and water emulsion of claim 8 wherein the plurality of target nucleic acids comprises a heavy chain nucleic acid and a light chain nucleic acid.

10. The oil and water emulsion of claim 8 wherein the plurality of target nucleic acids comprises a heavy chain cDNA and a light chain cDNA.

11. The oil and water emulsion of claim 8 wherein the plurality of target nucleic acids comprises mRNA, a polynucleotide encoding a T cell receptor component, a polynucleotide having an immune cell nucleic acid sequence, a polynucleotide encoding an HLA component, a polynucleotide comprising a sequence indicative of haplotype, a polynucleotide encoding a B cell receptor component, a heavy chain polynucleotide or a light chain polynucleotide.

12. The oil and water emulsion of claim 2 wherein the oil and water emulsion further comprises a plurality of second polynucleotides, wherein the plurality of second polynucleotides each comprise a sequence complementary to the universal primer region and an annealing primer region.

13. The oil and water emulsion of claim 1 wherein the sequencing primer region is 5' to the barcode and the universal primer region is 3' to the barcode.

14. The oil and water emulsion of claim 1 wherein the single cell is a B cell or T cell.

15. The oil and water emulsion of claim 1 wherein the single cell is a bacterial cell.

16. The oil and water emulsion of claim 1 wherein the single cell is an immune cell, a cell from a tumor, or a cell from a subject with a tumor.

17. The oil and water emulsion of claim 1 further comprising a plurality of cells, with each cell of the plurality being a single cell sequestered with one bead.

18. The oil and water emulsion of claim 1 further comprising a plurality of cells, with each cell of the plurality being a single cell sequestered with one bead having a unique barcode.

19. The oil and water emulsion of claim 1 wherein the barcode comprises from 4 nucleotides to 36 nucleotides.

20. A method comprising
creating an oil and water emulsion comprising a lysed single cell sequestered with one bead, wherein the one bead comprises a plurality of polynucleotides attached thereto wherein each polynucleotide of the plurality of polynucleotides includes a sequencing primer region, a barcode, and a universal primer region, wherein the sequencing primer region is for sequencing the polynucleotide, wherein the oil and water emulsion further comprises a second polynucleotide, wherein the second polynucleotide comprises a sequence complementary to the universal primer region and an annealing primer region, and wherein a plurality of target nucleic acids are annealed to annealing primer regions; and
reverse transcribing or extending the target nucleic acids to produce complementary strands including the barcode.

21. The method of claim 20 further comprising amplifying the complementary strands including the barcode.

22. The method of claim 20 further comprising amplifying and sequencing the complementary strands including the barcode.

23. The method of claim 20 further comprising amplifying and sequencing the complementary strands including the barcode and correlating at least one of the sequenced strands to a unique barcode.

24. The method of claim 20 wherein the oil and water emulsion comprises a plurality of lysed cells, with each lysed cell of the plurality being a single lysed cell sequestered with one bead, wherein the one bead comprises a plurality of polynucleotides attached thereto wherein each polynucleotide of the plurality of polynucleotides includes a sequencing primer region, a unique barcode, and a universal primer region, wherein the sequencing primer region is for sequencing the polynucleotide, wherein the oil and water emulsion further comprises a plurality of second polynucleotides, wherein the plurality of second polynucleotides comprises a sequence complementary to the universal primer region and an annealing primer region, wherein a plurality of target nucleic acids are annealed to annealing primer regions; and
reverse transcribing or extending the target nucleic acids to produce complementary strands including the unique barcode.

25. The method of claim 20 further comprising amplifying the complementary strands including the unique barcode.

26. The method of claim 20 further comprising amplifying and sequencing the complementary strands including the unique barcode.

27. The method of claim 20 further comprising amplifying and sequencing the complementary strands including the unique barcode and correlating at least one of the sequenced strands to the unique barcode.

28. The method of claim 20 wherein the plurality of target nucleic acids comprises a heavy chain nucleic acid and a light chain nucleic acid.

29. The method of claim 20 wherein the plurality of target nucleic acids comprises a heavy chain cDNA and a light chain cDNA.

30. The method of claim 20 wherein the plurality of target nucleic acids comprises mRNA, a polynucleotide encoding a T cell receptor component, a polynucleotide having an immune cell nucleic acid sequence, a polynucleotide encoding an HLA component, a polynucleotide comprising a sequence indicative of haplotype, a polynucleotide encoding a B cell receptor component, a heavy chain polynucleotide or a light chain polynucleotide.

31. The method of claim 20 wherein the sequencing primer region is 5' to the barcode and the universal primer region is 3' to the barcode.

32. The method of claim 20 wherein the lysed single cell is a B cell or T cell.

33. The method of claim 20 wherein the lysed single cell is a bacterial cell.

34. The method of claim 20 wherein the lysed single cell is an immune cell, a cell from a tumor, or a cell from a subject with a tumor.

35. The oil and water emulsion of claim 3 wherein the barcode of a first polynucleotide is a clonal copy of the barcode of an additional polynucleotide.

36. The method of claim 20 wherein the barcode of a first polynucleotide is a clonal copy of the barcode of an additional polynucleotide.

37. The method of claim 20 wherein the plurality of target nucleic acids includes a plurality of different target nucleic acids and the annealing primer regions includes a plurality of different annealing primer regions, wherein the plurality of different target nucleic acids are annealed to the plurality of different annealing primer regions.

38. The oil and water emulsion of claim 12 wherein at least two second polynucleotides of the plurality each comprise a different annealing primer region.

39. The oil and water emulsion of claim 12 wherein the different annealing primer regions each target a different target nucleic acid.

40. The oil and water emulsion of claim 1 wherein the annealing primer region is capable of hybridizing to a target nucleic acid.

* * * * *

```
                        SEQUENCE LISTING

<160> NUMBER OF SEQ ID NOS: 9

<210> SEQ ID NO 1
<211> LENGTH: 119
<212> TYPE: DNA
<213> ORGANISM: Artificial
<220> FEATURE:
<223> OTHER INFORMATION: primer

<400> SEQUENCE: 1
aatgatacgg cgaccaccga gatctacact ctttccctac acgacgctct tccgatctag      60
atcggaagag cggttcagca ggaatgccga gaccgatctc gtatgccgtc ttctgcttg     119

<210> SEQ ID NO 2
<211> LENGTH: 119
<212> TYPE: DNA
<213> ORGANISM: Artificial
<220> FEATURE:
<223> OTHER INFORMATION: primer

<400> SEQUENCE: 2
aatgatacgg cgaccaccga gatctacact ctttccctac acgacgctct tccgatctag      60
atcggaagag cggttcagca ggaatgccga gaccgatctc gtatgccgtc ttctgcttg     119

<210> SEQ ID NO 3
<211> LENGTH: 33
<212> TYPE: DNA
<213> ORGANISM: Artificial
<220> FEATURE:
<223> OTHER INFORMATION: primer

<400> SEQUENCE: 3
acactctttc cctacacgac gctcttccga tct                                   33

<210> SEQ ID NO 4
<211> LENGTH: 82
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (34)..(53)
<223> OTHER INFORMATION: n is a, c, g, or t

<400> SEQUENCE: 4
acactctttc cctacacgac gctcttccga tctnnnnnnn nnnnnnnnnn nnncagcttt      60
tttttttttt tttttttttt tt                                               82

<210> SEQ ID NO 5
<211> LENGTH: 33
<212> TYPE: DNA
<213> ORGANISM: Artificial
<220> FEATURE:
<223> OTHER INFORMATION: primer

<400> SEQUENCE: 5
acactctttc cctacacgac gctcttccga tct                                   33
```

```
<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
agatcggaag agcgtcgtgt a                                           21

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
aaaaaaaaaa aaaaaaaaaa aaaaacgac                                   29

<210> SEQ ID NO 8
<211> LENGTH: 82
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (30)..(49)
<223> OTHER INFORMATION: n is a, c, g, or t

<400> SEQUENCE: 8
aaaaaaaaaa aaaaaaaaaa aaaaagctgn nnnnnnnnnn nnnnnnnnna gatcggaaga    60
gcgtcgtgta gggaaagagt gt                                          82

<210> SEQ ID NO 9
<211> LENGTH: 103
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (34)..(53)
<223> OTHER INFORMATION: n is a, c, g, or t

<400> SEQUENCE: 9
acactctttc cctacacgac gctcttccga tctnnnnnnn nnnnnnnnnn nnncagcttt    60
tttttttttt tttttttttt ttatgtgctg cgagaaggct aga                   103
```